(12) United States Patent
Petersen et al.

(10) Patent No.: US 6,762,307 B2
(45) Date of Patent: Jul. 13, 2004

(54) METHOD FOR THE PREPARATION OF CITALOPRAM

(75) Inventors: Hans Petersen, Vanløse (DK); Jakob Felding, Charlottenlund (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/183,958

(22) Filed: Jun. 25, 2002

(65) Prior Publication Data

US 2003/0060641 A1 Mar. 27, 2003

Related U.S. Application Data

(63) Continuation of application No. PCT/DK99/00739, filed on Dec. 28, 1999.

(51) Int. Cl.[7] .................. C07D 307/78; C07D 307/87; C07D 217/00
(52) U.S. Cl. .................. 549/467; 549/469; 564/360
(58) Field of Search ................ 514/469; 549/469, 549/467; 564/360

(56) References Cited

U.S. PATENT DOCUMENTS

| | | | |
|---|---|---|---|
| 3,467,675 A | 9/1969 | Petersen et al. ......... | 260/346.2 |
| 4,136,193 A | 1/1979 | Bogeso et al. ............. | 424/285 |
| 4,650,884 A | 3/1987 | Bogeso .................... | 549/467 |
| 4,943,590 A | 7/1990 | Boegesoe et al. ........... | 415/469 |
| 5,296,507 A | 3/1994 | Tanaka et al. .............. | 514/465 |
| 6,020,501 A | 2/2000 | Massonne et al. .......... | 549/307 |
| 6,028,204 A | 2/2000 | Massonne et al. .......... | 549/307 |
| 6,229,026 B1 | 5/2001 | Petersen .................... | 549/467 |
| 6,258,842 B1 | 7/2001 | Petersen et al. ............ | 514/469 |
| 6,291,689 B1 | 9/2001 | Petersen et al. ............ | 549/467 |
| 6,310,222 B1 | 10/2001 | Ikemoto et al. ............. | 549/467 |
| 6,365,747 B1 | 4/2002 | Dall'Asta et al. ........... | 548/417 |
| 6,392,060 B2 | 5/2002 | Petersen et al. ............ | 549/307 |
| 6,403,813 B1 | 6/2002 | Petersen et al. ............ | 549/305 |
| 6,407,267 B1 | 6/2002 | Rock et al. ................ | 549/467 |
| 6,420,574 B2 | 7/2002 | Petersen et al. ............ | 549/467 |
| 6,426,422 B1 | 7/2002 | Petersen et al. ............ | 549/467 |
| 2002/0004604 A1 | 1/2002 | Petersen et al. ............ | 549/462 |
| 2002/0026062 A1 | 2/2002 | Petersen et al. ............ | 549/467 |
| 2002/0028956 A1 | 3/2002 | Weber ....................... | 549/307 |
| 2002/0035277 A1 | 3/2002 | Rock et al. ................ | 549/467 |
| 2002/0040153 A1 | 4/2002 | Petersen .................... | 549/467 |
| 2002/0061925 A1 | 5/2002 | Petersen et al. ............ | 514/469 |
| 2002/0077353 A1 | 6/2002 | Petersen et al. ............ | 514/469 |
| 2002/0087012 A1 | 7/2002 | Castellin et al. ............ | 549/467 |

FOREIGN PATENT DOCUMENTS

| | | | |
|---|---|---|---|
| EP | 1 095 926 | 5/2001 | .......... C07C/33/46 |
| WO | 98/19511 | 5/1998 | |
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | ......... C07D/307/87 |
| WO | 00/39112 | 7/2000 | ......... C07D/307/87 |
| WO | 00/44738 | 8/2000 | ......... C07D/307/88 |
| WO | 01/45483 | 6/2001 | |
| WO | 01/47877 | 7/2001 | |
| WO | 01/49672 | 7/2001 | ......... C07D/307/87 |
| WO | 01/51477 | 7/2001 | ......... C07D/307/87 |
| WO | 01/66536 | 9/2001 | ......... C07D/307/87 |

OTHER PUBLICATIONS

U.S. patent application Ser. No. 10/186,337, filed Jun. 27, 2002.

(List continued on next page.)

*Primary Examiner*—Rita Desai
*Assistant Examiner*—Raymond Covington
(74) *Attorney, Agent, or Firm*—Darby & Darby

(57) ABSTRACT

The present invention relates to a method for the preparation of citalopram or any of its enantiomers and acid addition salts thereof comprising reaction of a compound of formula II

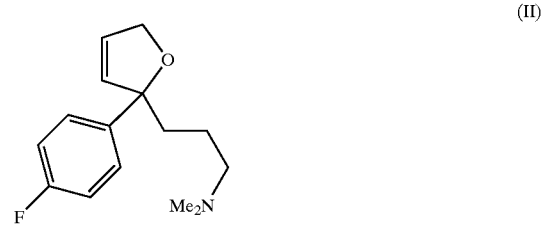

(II)

with a diene having the formula

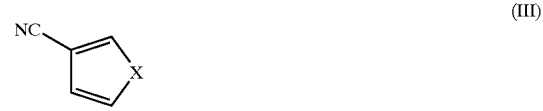

(III)

wherein X is O, S, SO$_2$, —N=N—, —CO—O—, —O—CO—, or or with a diene having the formula

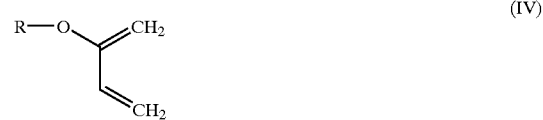

(IV)

wherein R is alkyl or optionally substituted aryl or arylalkyl.

The invention also relates to intermediates used in the new process for the preparation of citalopram, as well as citalopram prepared according to the new process.

9 Claims, No Drawings

OTHER PUBLICATIONS

U.S. patent application Ser. No. 10/191,808, filed Jul. 8, 2002.

Levy, L.F., "4–Aminophthalide and Some Derivatives", *J. Chem. Soc.* pp. 867–870 (1931).

Tirouflet J., "Phtalide Substitutes en 5", *Bull. Soc. Sci. de Bretagne* 26:35–43 (1951).

Bigler, Allan et al., "Quantitative Structure–activity Relationships in a Series of Selective 5–HT uptake inhibitors," *Eur. J. Med. Chem.* 3:289–295 (1997).

Forney L., "Reaction of Terephthalic Acid with Formaldehyde in Sulfur Trioxide Media," *J. Org. Chem.* 35:1695–1696 (1970).

Dordor et al., "Reaction of Oxazolines with Phosphorus Oxychloride," *Tetrahedron Letters* 24:1437–1440 (1983).

Barton et al., *Comprehensive Organic Chemistry. The Synthesis and Reactions of Organic Compounds*, vol. 2, pp. 1024–1025.

METHOD FOR THE PREPARATION OF CITALOPRAM

This application is a continuation of International application no. PCT/DK99/00739, filed Dec. 28, 1999. The disclosure of the prior application is hereby incorporated by reeference, in its entirety.

The present invention relates to a method for the preparation of the well known anti-depressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well-known antidepressant drug that has now been on the market for some years and has the following structure:

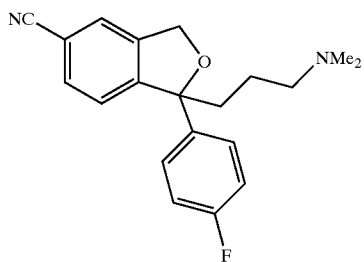

(I)

It is a selective, centrally acting serotonin (5-hydroxytryptamine; 5-HT) reuptake inhibitor, having antidepressant activities. The antidepressant activity of the compound has been reported in several publications, e.g. J. Hyttel, *Prog. Neuro-Psychopharmacol. & Biol. Psychiat.*, 1982, 6, 277–295 and A. Gravem, *Acta Psychiatr. Scand.*, 1987, 75, 478–486. The compound has also been disclosed to show effects in the treatment of dementia and cerebrovascular disorders, EP-A 474580.

Citalopram was first disclosed in DE 2,657,271 corresponding to U.S. Pat. No. 4,136,193. This patent publication describes the preparation of citalopram by one method and outlines a further method that may be used for preparing citalopram.

According to the process described, the corresponding 1-(4-fluorophenyl)-1, 3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the second method, which is only outlined in general terms, citalopram may be obtained by ring closure of the compound:

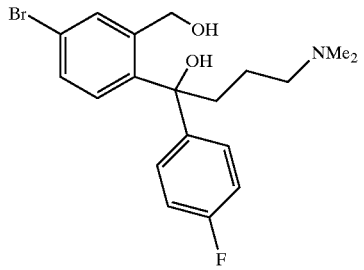

in the presence of a dehydrating agent and subsequent exchange of the 5-bromo group with cyano using cuprous cyanide. The starting material of formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884 according to which an intermediate of the formula

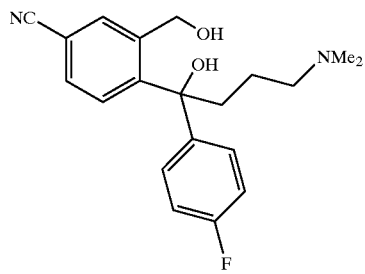

is subjected to a ring closure reaction by dehydration with strong sulfuric acid in order to obtain citalopram. The intermediate of formula III was prepared from 5-cyanophthalide by two successive Grignard reactions, i.e. with 4-fluorophenyl magnesium halogenide and N,N-dimethylaminopropyl magnesium halogenide, respectively.

Further processes are disclosed in International patent application Nos. WO 98/019511, WO 98/019512 and WO 98/019513. WO 98/019512 and WO 98/019513 relate to methods wherein a 5-amino-, 5-carboxy- or 5-(sec. ammocarbonyl)phthalide is subjected to two successive Grignard reactions, ring closure and conversion of the resulting 1,3-dihydroisobenzofuran derivative to the corresponding 5-cyano compound, i.e. citalopram. International patent application No. WO 98/019511 discloses a process for the manufacture of citalopram wherein a (4-substituted-2-hydroxymethylphenyl-(4-fluorphenyl)methanol compound is subjected to ring closure and the resulting 5-substituted 1-(4-fluorophenyl)-1,3-dihydroisobenzofuran converted to the corresponding 5-cyano derivative and alkylated with a (3-dimethylamino)propylhalogenide in order to obtain citalopram.

Finally, methods of preparing the individual enantiomers of citalopram are disclosed in U.S. Pat. No. 4,943,590 from which it also appears that the ring closure of the intermediate of formula III may be carried out via a labile ester with a base.

It has now been found that citalopram may be obtained by a new process in which the citalopram skeleton is formed by Diels-Adler reaction of a dihydrobenzofurane with a diene.

SUMMARY OF THE INVENTION

Accordingly, the present invention relates to a novel method for the preparation of citalopram, its enantiomers and acid addition salts thereof comprising:

Reaction of a compound of formula

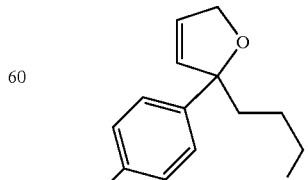

(II)

with a) a diene having the formula III

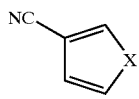

(III)

wherein X is selected from O, S, SO$_2$, —N=N—, —CO—O— and —O—CO—, followed by oxidation to form citalopram,
or with
b) a compound of formula

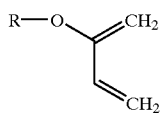

(IV)

wherein R is alkyl, or optionally substituted aryl or arylalkyl, followed by conversion of the resulting compound of formula

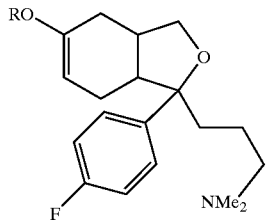

(V)

wherein R is as defined above to a compound of formula

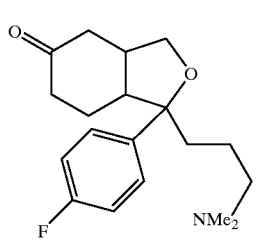

(VI)

which is converted to a compound of formula

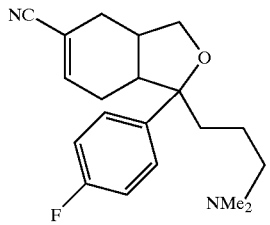

(VII)

followed by oxidation of the compound of formula VII to form citalopram.

The reaction of the compound of formula II with the diene of formula III is carried out using the conventional reaction conditions for carrying out reactions of the Diels-Adler type. Thus, the reaction is suitably carried out in a solvent, such as benzene, toluene, 1, 3,5-trimethylbenzene; at a temperature between 60 and 180° C., preferably at reflux.

Initial reaction of the compound of formula II with the diene of formula III leads to the formation of the intermediate having the formula

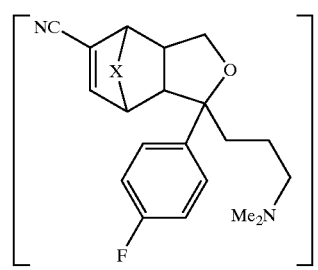

(II')

wherein X is as defined above.

Oxidation of the intermediate of formula II' leads to the formation of citalopram.

The oxidation of the intermediate of formula II' is carried out in presence of oxygen and agents such as Pd/C, S, dideoxyquinon, and chloranil.

In some cases, i.e. where the compound of formula III is a 3-cyanofuran, the conversion of the intermediate of formula II' to citalopram is carried out in presence of a Lewis acid or a mineral acid. Suitable Lewis acids include ZnCl$_2$, TiCl$_4$, BF$_3$ Et$_2$O etc. Suitable mineral acids include hydrochloric acid, sulfuric acid etc.

When the compound of formula III used in the process is the 3-cyanofuran, the intermediate of formula II' may be isolated.

The reaction of the compound of formula II with the compound of formula IV is carried out using the conventional reaction conditions for carrying out reactions of the Diels-Adler type. Thus, the reaction is suitably carried out in an inert solvent, such as benzene, toluene, 1, 3,5-trimethylbenzene; at a temperature between 60 and 180° C., preferably at reflux. The aryl and arylalkyl substituents R in formula IV may be substituted with substituents such as halogen, alkyl, alkoxy, etc.

The conversion of the compound of formula V to a compound of formula VI is suitably carried out in an aqueous acidic media or in an aqueous alkaline media.

The introduction of the cyano group into the compound of formula VI, is suitably carried out by reaction of a compound of formula VI with NaCN, KCN, or TMSCN in an aqueous media followed by dehydration using conventional dehydrating agents such as thionylchloride, POCl$_3$, P$_2$O$_5$ or a Vilsmeier reagent. When TMSCN is used, the reaction is suitably carried out in presence of a Lewis acid such as ZnCl$_2$, ZnI$_2$ or BF$_3$, Et$_2$O.

The compound of formula VII is oxidised to form citalopram in presence of oxygen and agents such as Pd/C, dideoxyquinon, chloranil etc.

In a further aspect, the invention relates to the above processes in which the compound of formula II is used in the form of the S-enantiomer.

In yet another aspect, the present invention relates to citalopram and S-citalopram manufactured by the process of the invention, and an antidepressant pharmaceutical composition comprising citalopram or S-citalopram manufactured by the process of the invention.

According to the present invention, the compound of formula II may be prepared from a 4-fluorobenzoic acid derivative and transformed to citalopram and its salts by a process, comprising:

i) Reaction of a 4-fluorobenzoic acid of the formula VIII

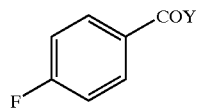
(VIII)

wherein Y is halogen, especially chloro, —O-alkyl, —NR'R" wherein R' and R" are selected from hydrogen, alkyl, alkoxy or R' and R" together form a ring, with M⁺, ⁺C≡C—CH₂—O—Z, wherein M⁺ is a metal ion and Z is a protection group or hydrogen, followed by removal of the protecting group Z;

ii) reacting the resulting compound of formula IX

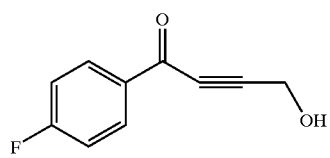
(IX)

with a Grignard reagent having the formula HalMg(CH₂)₃NMe₂ wherein Hal is chloro or bromo;

iii) reduction of the resulting compound of formula

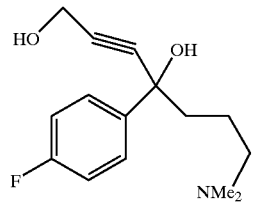
(X)

to form a compound of formula

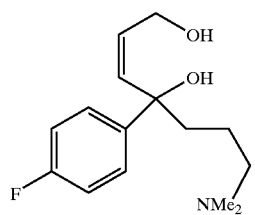
(XI)

which is treated with a dehydrating agent to form a compound of formula II.

The reaction of the compound of formula VIII with M⁺, ⁺C≡C—CH₂—OZ is suitably carried out in tetrahydrofuran, Et₂O or toluene. Suitable protecting groups Z include tetrahydropyran, trialkylsilyl, etc. The protecting group is removed according to conventional methods for removal of protecting groups.

Reaction of the compound of formula IX with the Grignard reagent is carried out using conventional reaction conditions for Grignard reactions. Suitable solvents for Grignard reactions include tetrahydrofuran, Et₂O and toluene.

Reduction of the compound of formula X is carried out in water or ethanol using Raney-Ni or a Lindlar catalyst as the reducing agent.

Treatment of the compound of formula XI with a dehydrating agent is suitably carried out in toluene, EtOAc or tetrahydrofuran. Suitable dehydrating agents include tosylchloride, methanesulfonylchloride etc.

Alternatively, the compound of formula II may be prepared from 4-fluorobenzaldehyde and transformed to citalopram and its salts by a process, comprising:

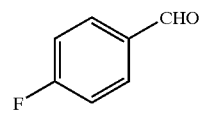
(XII)

iv) reaction of 4-fluorobenzaldehyde of the formula with M⁺, ⁺C≡C—CH₂—O—Z, wherein M⁺ is a metal ion and Z is a protection group or hydrogen; followed by v) oxidation of the resulting compound of formula XIII

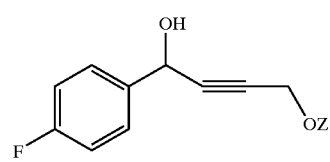
(XIII)

and removal of the protecting group Z to form

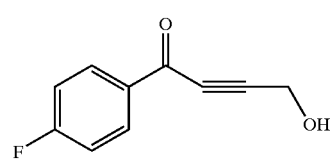
(IX)

vi) reaction of the compound of formula IX with a Grignard reagent having the formula HalMg(CH₂)₃NMe₂ wherein Hal is chloro or bromo; followed by conversion of the compound of formula X to the compound of formula II as described above.

The reaction of the compound of formula XII with M⁺, ⁺C≡C—CH₂—OZ is suitably carried out in tetrahydrofuran, Et₂O or toluene. The protecting group Z may be tetrahydropyran trialkylsilyl etc.

Oxidation of the compound of formula XIII is carried out in presence of oxygen, suitably in presence of agents such as Pd/C, DDQ, chloranil etc.

The protecting group Z is removed according to conventional methods for removal of protecting groups.

According to a third embodiment of the invention, the compound of formula II may also be prepared from dimethyl aminopropyl-4-fluorobenzophenon and transformed to citalopram and its salts by a process, comprising:

viii) reaction of a compound of formula

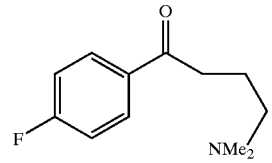
(XIV)

with a Grignard reagent having the formula HalMgCCCH₂OMgHal wherein Hal is chloro or bromo; followed by conversion of the resulting compound of formula X to a compound of formula II as described above.

Reaction of the compound of formula XIV with the Grignard reagent is carried out using conventional reaction conditions for Grignard reactions. Suitable solvents for Grignard reactions include tetrahydrofuran, Et$_2$O and toluene.

According to a preferred embodiment of the invention, the diene of formula III used for the preparation of citalopram is selected from 3-cyanofurane, 3-cyano-thiophen 1,1-dioxide, 4-cyano-pyridazine and 2-oxa-2H-pyran-5-carbonitril.

The total synthesis of citalopram as outlined above, comprises the use of novel intermediates for the preparation of citalopram. The novel intermediates of formula (II), (XI) and (X) illustrated above also form part of the present invention.

The starting materials of formula III are known or may be prepared by conventional methods.

Thus, 3-cyano-furan is a known compound which may be prepared from the corresponding 3-bromo-furan, 3-formyl-furan or 3-carboxy-furan using conventional methods.

3-cyano-thiophene 1,1-dioxide may be prepared by oxidation of 3-cyano-thiophene, using e.g peroxide. The 3-cyano-thiophene is known from the literature and can be prepared from the corresponding 3-bromo-, 3-formyl- and 3-carboxy-thiophenes.

4-cyano-pyridazine can be prepared by oxidation of benzopyridazine using e.g. KMnO$_4$ as the oxidation agent, followed by decarboxylation of the resulting pyridazine-4,5-dicarboxylic acid and conversion of the carboxylic acid to a nitrile using conventional methods.

2-Oxa-2H-pyran-5-carbonitrile can be prepared from the corresponding carboxylic acid using conventional methods for the conversion of a carboxy group to a cyano group. 2-Oxa-2H-pyran-5-carboxylic acid can be prepared as described in Organic Synthesis, IV, pp. 201–202.

The intermediates of formula II, X, XI, XIII in the form of enantiomers, may be obtained using conventional separation techniques or as described in U.S. Pat. No. 4,943,590.

It is advantageous to treat the compounds with an optically active acid, for example with (−)- or (+)-tartaric acid or (−)- or (+)-camphor-10-sulfonic acid, in order to separate the diastereoisomeric salt mixture and to isolate the optically active compound as free base or as a salt thereof.

The salts of the compounds (II), (X) and (XI), may be any acid addition salt, including pharmaceutically acceptable acid addition salts mentioned above, for example the hydrochloride, hydrobromide, etc.

The compound of general formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds of the invention may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate, or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, etc.

What is claimed is:

1. A method for the preparation of citalopram or any of its enantiomers and acid addition salts thereof comprising reaction of a compound of formula

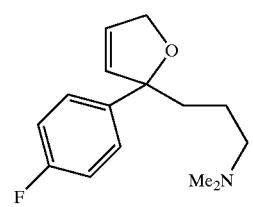

(II)

with a) a diene having the formula

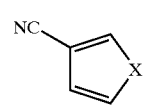

(III)

wherein X is O, S, SO$_2$, —N=N—, —CO—O—, or —O—CO—; followed by oxidation to form citalopram; or with b) a compound of formula

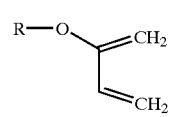

(IV)

wherein R is alkyl or optionally substituted aryl or arylalkyl, followed by conversion of the resulting compound of formula

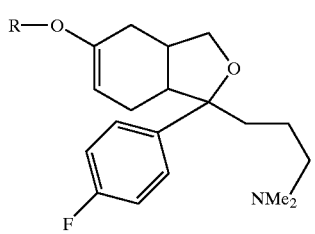

(V)

wherein R is as defined above, to a compound of formula

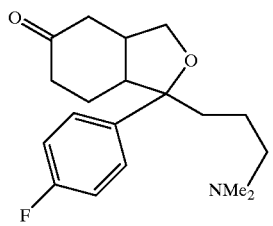

(VI)

which is converted to a compound of formula

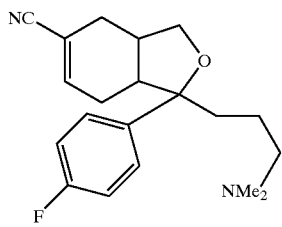

(VII)

followed by oxidation of the compound of formula VII to form citalopram;

and thereafter optionally converting the free base or an acid addition salt of citalopram, thus obtained, to a pharmaceutically acceptable salt thereof.

2. The method according to claim 1, wherein the compound of formula II is prepared by i) reaction of a 4-fluorobenzoic acid derivative of the formula

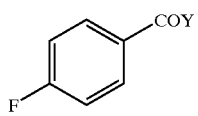

(VIII)

wherein Y is halogen, —O-alkyl, —NR'R" wherein R' and R" are selected from hydrogen, alkyl, alkoxy or R' and R" together form a ring, with $M^+$, $^+C{\equiv}C{-}CH_2{-}O{-}Z$, wherein $M^+$ is a metal ion and Z is a protection group or hydrogen, followed by removal of the protecting group Z; and ii) reaction of the resulting compound of formula IX

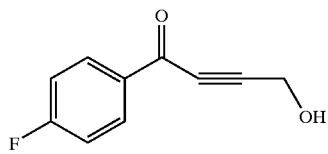

(IX)

with a Grignard reagent having the formula $HalMg(CH_2)_3NMe_2$ wherein Hal is chloro or bromo;

iii) reduction of the resulting compound of formula

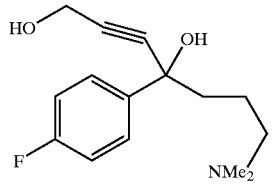

(X)

to form a compound of formula

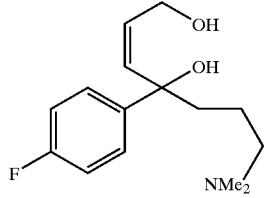

(XI)

which is treated as a dehydrating agent agent to form a compound of formula II.

3. The method according to claim 1, wherein the compound of formula II is prepared by vi) reaction of 4-fluorobenzaldehyde of the formula XII

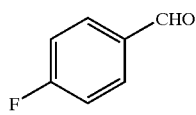

(XII)

with $M^+$, $^+C{\equiv}C{-}CH_2{-}O{-}Z$, wherein $M^+$ is a metal ion and Z is a protection group or hydrogen;

v) oxidation of the resulting compound of formula XIII

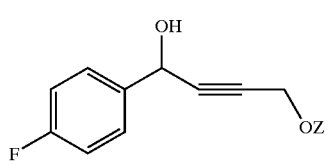

(XIII)

and removal of the protecting group Z to form a compound of formula IX (IX)

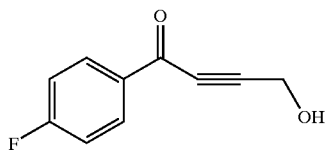

vi) reaction of the compound of formula IX with a Grignard reagent having the formula HalMg(CH$_2$)$_3$NMe$_2$ wherein Hal is chloro or bromo;

vii) reduction of the resulting compound of formula (X)

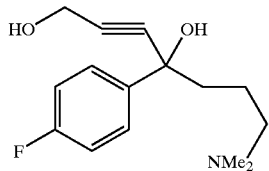

to form a compound of formula (XI)

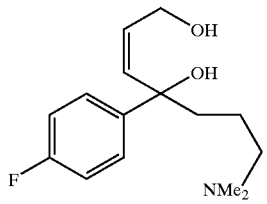

which is treated with a dehydrating agent to form a compound of formula II.

4. The method according to claim 1, wherein the compound of formula II is prepared by viii) reaction of a compound of formula (XIV)

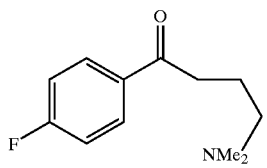

with a Grignard reagent having the formula HalMgCCCH$_2$OMgHal, wherein Hal is chloro or bromo;

vix) reduction of the resulting compound of formula (X)

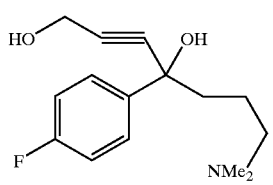

to form a compound of formula (XI)

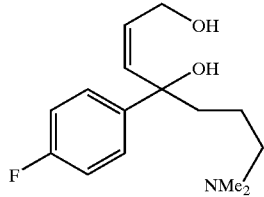

which is treated with a dehydrating agent to form a compound of formula II.

5. A compound selected from (X)

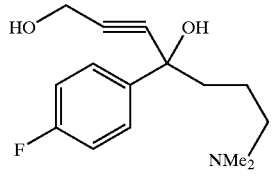

and any of its enantiomers and acid addition salts thereof.

6. A compound selected from (XI)

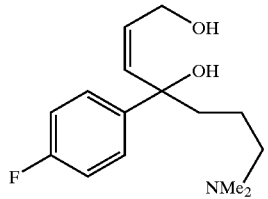

and any of its enantiomers and acid addition salts thereof.

7. A compound selected from (II)

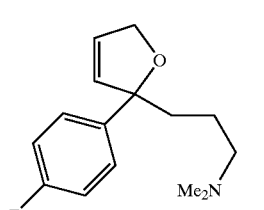

and any of its enantiomers and acid addition salts thereof.

8. A method according to claim 1 wherein the compound II is used in the form of the S-enantiomer.

9. A method according to claim 2, wherein Y is chloro.

* * * * *